(12) United States Patent
Dees et al.

(10) Patent No.: US 7,384,623 B1
(45) Date of Patent: *Jun. 10, 2008

(54) HIGH ENERGY PHOTOTHERAPEUTIC AGENTS

(75) Inventors: H. Craig Dees, Knoxville, TN (US); Timothy Scott, Knoxville, TN (US); John T. Smolik, Loudon, TN (US); Eric A. Wachter, Oak Ridge, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,622

(22) Filed: Aug. 25, 1999

Related U.S. Application Data

(62) Division of application No. 09/216,787, filed on Dec. 21, 1998, now Pat. No. 6,331,286.

(51) Int. Cl.
*A61B 5/055* (2006.01)

(52) U.S. Cl. .................. 424/9.37; 424/1.11; 424/1.13; 424/1.17; 424/1.33; 424/1.37; 424/1.57; 424/1.85; 424/9.2; 424/9.4; 424/9.45; 436/35; 436/57; 436/58; 436/63; 436/64; 436/125

(58) Field of Classification Search ........... 424/1.11, 424/1.13, 1.33, 1.81, 1.85, 9.4, 9.45, 1.17, 424/1.29, 1.53, 1.73, 9.2, 1.37, 1.57; 436/56, 436/57, 64, 813, 968, 829, 58, 63, 35, 125; 549/388; 514/12
See application file for complete search history.

(56) References Cited

U.S. PATENT DOCUMENTS

| | | | |
|---|---|---|---|
| 3,868,950 A | 3/1975 | Kato | 128/66 |
| 3,986,513 A | 10/1976 | Stuhl | 128/373 |
| 4,066,650 A | 1/1978 | Egyud | 260/281 G |
| 4,172,979 A | 10/1979 | Morrison | 250/505 |
| 4,241,060 A | 12/1980 | Smithen | 424/248.57 |
| 4,282,232 A | 8/1981 | Agrawal | 424/267 |
| 4,371,540 A | 2/1983 | Lee et al. | 424/273 R |
| 4,444,189 A | 4/1984 | Seiverd | 128/395 |
| 4,462,992 A | 7/1984 | Agrawal et al. | 424/180 |
| 4,490,543 A | 12/1984 | Berquist et al. | |
| 4,599,227 A | 7/1986 | Dees et al. | 424/38 |

(Continued)

FOREIGN PATENT DOCUMENTS

EP   0 097 012   * 12/1983

(Continued)

OTHER PUBLICATIONS

Serafini et al. Iodine-123-Rose Bengal: An improved hepatobiliary imaging agent, Journal of Nuclear Medicine, 16(7): 629-632 (1975).*

The Merck Index, Tenth Edition (1983), Windhotz et al. (eds), p. 8138.*

Bezman, S.A. et al, "Photodynamic Inactivation of *E. coli* by Rose Bengal Immobilized on Polystyrene Beads," Biochemistry and Photobiology, vol. 28, pp. 325-329, 1978.

Fluhler, E.N. et al, "Laser Intensity and Wavelength Dependence of Rose Bengal Photosensitized Inhibition of Red Blood Cell Acetylcholinesterase," Biochimica et Biophysica Acta, 990, pp. 269-275, 1989.

(Continued)

*Primary Examiner*—Gailene Rio Gabel
(74) *Attorney, Agent, or Firm*—Cook, Alex, McFarron, Manzo, Cummings & Mehler, Ltd.

(57) ABSTRACT

High energy phototherapeutic agents or radiosensitizer agents comprised of a halogenated xanthene, or other related agents that exhibit a preference for concentration in biologically sensitive structures in diseased tissue, and methods of treating and imaging using such radiosensitizer agents in such diseased tissue are described herein.

9 Claims, 3 Drawing Sheets

U.S. PATENT DOCUMENTS

| | | | |
|---|---|---|---|
| 4,647,578 A | 3/1987 | Crounse et al. | |
| 4,652,562 A | 3/1987 | Berenyi nee Poldermann | 514/237 |
| 4,681,091 A | 7/1987 | Picker et al. | 128/1 R |
| 4,691,332 A | 9/1987 | Burstein et al. | 378/7 |
| 4,820,258 A | 4/1989 | Mondain-Monval | 600/1 |
| 4,846,789 A * | 7/1989 | Heitz et al. | 604/522 |
| 4,856,528 A | 8/1989 | Yang et al. | 128/653 |
| 4,880,821 A | 11/1989 | Saari | 514/331 |
| 4,897,423 A | 1/1990 | Saari et al. | 514/603 |
| 4,921,963 A | 5/1990 | Skov et al. | 548/101 |
| 4,927,941 A | 5/1990 | Kagiya et al. | 548/264.8 |
| 4,945,102 A | 7/1990 | Suzuki et al. | 514/398 |
| 4,954,515 A | 9/1990 | Suto | 514/398 |
| 4,957,481 A | 9/1990 | Gatenby | |
| 4,973,848 A | 11/1990 | Kolobanov et al. | 250/458.1 |
| 4,977,273 A | 12/1990 | Kagiya et al. | 548/339 |
| 5,008,907 A | 4/1991 | Norman et al. | 378/65 |
| 5,019,368 A | 5/1991 | Epstein et al. | 424/1.1 |
| 5,026,694 A | 6/1991 | Skov et al. | 514/184 |
| 5,036,089 A | 7/1991 | Suto | 514/376 |
| 5,036,096 A | 7/1991 | Suto | 514/398 |
| 5,053,006 A | 10/1991 | Watson | 604/52 |
| 5,064,849 A | 11/1991 | Suzuki et al. | 514/383 |
| 5,128,139 A | 7/1992 | Brown et al. | 424/450 |
| 5,147,652 A | 9/1992 | Egyud | 424/450 |
| 5,149,801 A | 9/1992 | Kahl et al. | 540/145 |
| 5,175,287 A | 12/1992 | Lee et al. | 544/183 |
| 5,215,738 A | 6/1993 | Lee et al. | 424/10 |
| 5,225,182 A * | 7/1993 | Sharma | 424/9 |
| 5,270,330 A | 12/1993 | Suzuki et al. | 514/398 |
| 5,284,831 A | 2/1994 | Kahl et al. | 514/21 |
| 5,294,715 A | 3/1994 | Papadopoulou-Rosenzweig et al. | 546/106 |
| 5,302,369 A | 4/1994 | Day et al. | 424/1.29 |
| 5,304,654 A | 4/1994 | Kagiya et al. | 548/327.5 |
| 5,342,959 A | 8/1994 | Beylin et al. | 548/327.5 |
| 5,457,183 A | 10/1995 | Sessler et al. | 534/11 |
| 5,481,000 A | 1/1996 | Beylin et al. | 548/229 |
| 5,543,527 A | 8/1996 | Beylin et al. | 548/110 |
| 5,567,765 A | 10/1996 | Moore et al. | 524/801 |
| 5,576,013 A * | 11/1996 | Williams et al. | 424/423 |
| 5,591,422 A | 1/1997 | Hemmi et al. | 424/362 |
| 5,599,923 A | 2/1997 | Sessler et al. | 540/145 |
| 5,601,802 A | 2/1997 | Hemmi et al. | 424/9.36 |
| 5,602,142 A | 2/1997 | Papadopoulou-Rosenzweig | 514/290 |
| 5,616,584 A | 4/1997 | Lee et al. | 514/243 |
| 5,622,946 A | 4/1997 | Sessler et al. | 514/185 |
| 5,624,925 A | 4/1997 | Lee et al. | 514/243 |
| 5,641,764 A | 6/1997 | Martin et al. | 514/80 |
| 5,654,423 A | 8/1997 | Kahl et al. | 540/145 |
| 5,659,048 A | 8/1997 | Beylin et al. | 548/327.5 |
| 5,676,928 A | 10/1997 | Klaveness et al. | 424/9.321 |
| 5,700,825 A | 12/1997 | Hofer et al. | 514/397 |
| 5,733,572 A | 3/1998 | Unger et al. | 424/450 |
| 5,780,052 A * | 7/1998 | Khaw et al. | 424/450 |
| 5,780,653 A | 7/1998 | Tao et al. | 549/510 |
| 5,807,231 A | 9/1998 | Liprie | 600/3 |
| 5,827,186 A | 10/1998 | Chen et al. | 600/407 |
| 5,829,448 A | 11/1998 | Fisher et al. | 128/898 |
| 5,832,931 A | 11/1998 | Wachter et al. | 128/898 |
| 5,998,597 A | 12/1999 | Fisher et al. | 536/23.1 |
| 6,042,603 A | 3/2000 | Fisher et al. | 607/89 |
| 6,331,286 B1 | 12/2001 | Dees et al. | |

FOREIGN PATENT DOCUMENTS

| | | |
|---|---|---|
| JP | 06-128128 * | 10/1994 |
| WO | WO 96/07431 | 3/1996 |
| WO | WO 97/03697 | 2/1997 |
| WO | WO 97/26920 | 7/1997 |
| WO | WO 00/25819 | 5/2000 |
| WO | WO 00/25829 | 5/2000 |

OTHER PUBLICATIONS

Huang, A.J.W. et al, "Photothrombosis of Cornial Neovascularization by Intravenous Rose Bengal and Argon Laser Irradiation," Arch Opthalmol, vol. 106, pp. 680-685, May 1988. Neckers, D.C., "Rose Bengal," Journal of Photochemistry and Photobiology, A. Chemistry, vol. 47, pp. 1-29, 1989.

Neckers, D.C., "Rose Bengal," Journal of Photochemistry and Photobiology, A. Chemistry, vol. 47, pp. 1-29, 1989.

Norman, A. et al, "X-Ray Phototherapy for Solid Tumors," Acad Radiol, vol. 5, (suppl 1) pp. s177-179, Apr. 1998.

Norman, A. et al, "Point/Counterpoint: Radiation Doses in Radiation Therapy are not Safe," Med. Phys. vol. 24 (11), pp. 1710-1713, Nov. 1997.

Matsudaira, H. et al, "Iodine Contrast Medium Sensitizes Cultured Mammalian Cells to X Rays but not to Gamma Rays," Radiation Research, vol. 84, pp. 144-148, 1980.

Norman, A. et al, "Iodinated Contrast Agents for Brain Tumor Localization and Radiation Dose Enhancement," Invest. Radiol, vol. 26, pp. s120-1221, 1991.

Rubin, D. et al, "Nanoparticulate Contrast Media, Blood-Pool and Liver-Spleen Imaging," Investigative Radiology, vol. 29, suppl. 2, pp. s280-283, 1994.

Budavari, S., ed. et al, *The Merck Index*, Merck & Co., Inc., 11th ed., p. 4943, 1989.

Iwamoto, K.S. et al, "Radiation Dose Enhancement Therapy with Iodine in Rabbit VX-2 Brain Tumors," Radiation Therapy and Oncology, vol. 8, pp. 161-170, 1987.

Miller, R.W. et al, "Evaluation of Incorporated Iododeoxyuridine Cellular Radiosensitization by Photon Activation Therapy," Int. J. Radiation Oncology, Biol. Phys., vol. 13, pp. 1193-1197, 1987.

Zajusz, A. et al, "Normobaric Oxygen as a Sensitizer in Radiotherapy for Advanced Head and Neck Cancer," Neoplasma, vol. 42, No. 3, pp. 137-140, 1995.

United States Statutory Invention Registration No. H505 to Slatkin et al, for Boron Uptake in Tumors, Cerebrum and Blood From [$^{10}$B]NA$_4$B$_{24}$H$_{22}$S$_2$, published Aug. 2, 1988.

Mello, R.S. et al, "Radiation Dose Enhancement in Tumors with Iodine," *Medical Physics*, vol. 1, No. 1, pp. 75-78, Jan./Feb. 1983.

Norman, A. et al, "X-Ray Phototherapy for Canine Brain Masses," *Radiation Oncology Investigations*, vol. 5, pp. 8-14, 1997.

Serafini et al, IOdine-123-Rose Bengal: An Improved Hepatobiliary Imaging Agent, Journal of Nuclear Medicine, 1990.

Fisher et al, "Clinical and Preclinical Photodynamic Therapy," *Lasers in Surgery and Medicine*, vol. 17, pp. 2-31, 1995.

Young, S. et al, "Gadolinium(III) Texaphyrin: A Tumor Selective Radiation Sensitizer that is Detectable by MRI," Proc. Natl. Acad. Sci., vol. 93, pp. 6610-6615, Jun. 1996.

Bernhard, E.J. et al, "Re-Evaluating Gadolinium(III) Texaphyrin as a Radiosensitizing Agent," *Cancer Research*, vol. 60, pp. 86-91, Jan. 1, 2000.

Wilson et al., "Enhancement of Tumor Radiation Response by the Anivascular Agent 5,6-Dimethylxanthenone-4-Acetic Acid,", 1998. Int. J. Radiation Oncology Biol. Phys., vol. 42, No. 4, pp. 905-908, (1998).

American Association of Textile Chemists and Colorists, "Colour Index," Third Edition, 1971, pp. 4417-4430, vol. 4, published by The Society of Dyers and Colourists, Great Britain.

Xanthenes: Fluorone Derivatives, The Journal of Organic Chemistry 57 Jul. 31, 1992, No. 16, Washington, DC pp. 4418-4421.

(Svensk Farmaceutisk Tidskrift (1973) 77 (13): 641-647 (Abstract).

Office Action dated Dec. 3, 2004 for U.S. Appl. No. 09/817,448.

* cited by examiner

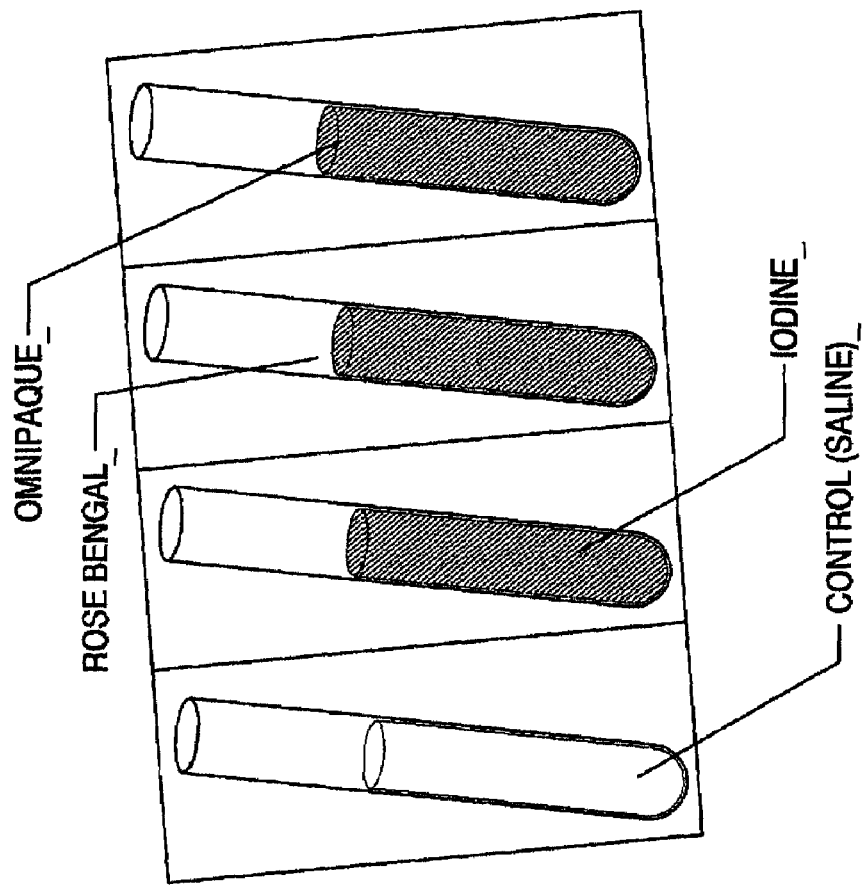
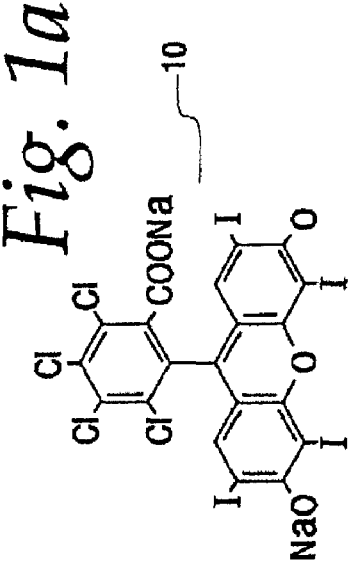
Fig. 1a
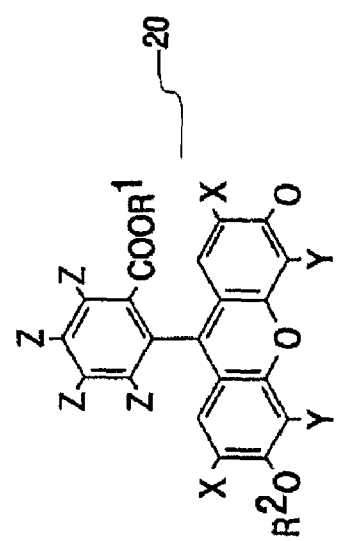
Fig. 1b
Fig. 2

HIGH ENERGY PHOTOTHERAPEUTIC AGENTS

This application is a divisional of U.S. Ser. No. 09/216,787 filed on Dec. 21, 1998 now U.S. Pat. No. 6,331,286.

BACKGROUND OF THE INVENTION

The present invention is directed to high energy phototherapeutic agents, or specifically to radiosensitizing and methods of treating and imaging using such phototherapeutic or radiosensitizer agents. More specifically, the treating and imaging is of diseased tissue, such as tumors, particularly cancerous tumors.

Diseased tissue or tumors, such as those for cancer, are often treated using ionizing radiation, in a process known as radiation therapy.

Radiation therapy (which typically uses electromagnetic radiation with energies of 1 keV or higher) for cancer typically works by attacking rapidly growing cells with highly penetrating ionizing radiation. Use of such radiation is attractive due to its ability to penetrate deeply into tissue, especially when diseased tissue is, or is located within, bone or other dense or opaque structures. Unfortunately, using rapid growth as the sole targeting criterion does not limit the effects of such treatment to cancer cells.

As a result, improvements have been made in the methods for delivery of the ionizing radiation to the site of the cancerous tumor so as to limit the effects of such radiation to the general area of the cancerous tumor. However, since healthy tissue and cancerous tissue typically have a similar biological response to radiation, a need exists to improve the potency of (or biological response to) the delivered radiation within and in the vicinity of the tumor, while not affecting the surrounding healthy tissue.

As an alternative to the use of ionizing radiation, photodynamic therapy (PDT) has been developed and shows considerable promise for treatment of a variety of cancers. Photodynamic therapy is the combination of a photosensitive agent with site-specific illumination (using non-ionizing, optical radiation) to produce a therapeutic response in diseased tissue, such as a tumor. In PDT, a preferential concentration of photosensitizer is to be located in the diseased tissue, either through natural processes or via localized application, and not in the healthy surrounding tissue. This provides an additional level of tissue specificity relative to that achievable through standard radiation therapy since PDT is effective only when a photosensitizer is present in tissue. As a result, damage to surrounding, healthy tissue can be avoided by controlling the distribution of agent. Unfortunately, when using conventional methods for the illumination step in PDT (1) the light required for such treatment is unable to penetrate deeply into tissue, and (2) the physician has minimal spatial control of the treatment site. This is particularly troublesome whenever the diseased tissue or tumor is deeply seated or located within bone or other opaque structures. Some of the inventors of the present invention have been able to resolve many of these problems for PDT, as shown in commonly-assigned U.S. Pat. No. 5,829,448.

Others, however, have focused their efforts on developing agents that are sensitized or activated by the ionizing radiation mentioned above. Potentially, the use of such radiation would enable treatment of more deeply seated diseased tissue than that possible with optical radiation. The agents used with such radiation are known as radiosensitizers. It is also desirable to achieve preferential concentration of the radiosensitizer in the diseased tissue, either through natural processes or via localized application, so as to provide additional specificity relative to that achievable through standard radiation therapy. The desired result is for radiation to become more efficacious when the radiosensitizer is present in tissue, so that less radiation is needed to treat the lesion tumor or other diseased tissue, and accordingly, potential damage to surrounding healthy tissue, resulting from collateral exposure to the radiation, is reduced. Hence, safety and efficacy would then be improved.

The ultimate success or failure of the radiosensitizer approach depends on: (1) therapeutic performance of agents, and (2) disease specificity in the site of activation. Currently used agents and targeting approaches, however, have had unacceptable results in each of these categories.

The therapeutic performance of a radiosensitizer is primarily a function of enhanced absorption of the applied radiation dose in sensitized tissues relative to that in non-sensitized tissues. This differential absorption is commonly effected by use of agents having a high absorption cross-section for a particular type of radiation (such as x-rays). For example, metal or halogen atoms are often used, either in atomic form or incorporated into a molecular carrier, due to their high x-ray cross-section. Absorption of x-rays by such atoms appears to lead to secondary radiative emissions, ionization, and other chemical or physical processes that increase the localized cytotoxicity of the applied energy (i.e., radiation-induced cell death, or "light cytotoxicity").

However, a high light cytotoxicity is not enough to make an agent an acceptable agent. The agents must also have a negligible effect when energy is not applied (i.e., have a low toxicity in the absence of radiation, or "dark cytotoxicity"). Unfortunately, many agents presently under investigation as radiosensitizers have the disadvantage of either: (a) a relatively high dark cytotoxicity or (b) a low light (cytotoxicity)-to-dark cytotoxicity ratio which limits their effectiveness and acceptability. Agents having a high light-to-dark cytotoxicity ratio are desirable because they (1) can be safely used over a range of dosages, (2) will exhibit improved efficacy at the treatment site (due to the compatibility with use at higher dosages as a consequence of their relative safety), and (3) will be better tolerated throughout the patient's body.

An additional problem with many current radiosensitizers is that the agent does not achieve significant preferential concentration in tumors. Specifically, most radiosensitizer targeting has been based on physical targeting, such as diffusion into tumors through leaky neurovasculature, which ultimately succeed or fail based on permeability of the tumor to agents that are aqueously soluble or are in a suspension formulation. As a result, large doses of the agent typically need to be administered, either locally or systemically, so as to saturate all tissues, hopefully reaching a therapeutic level in the desired treatment region or target. After such agent administration, a patient has to wait a clearance time of hours to days to allow excess agent to hopefully clear from healthy living tissues surrounding the desired treatment site. Thereafter, irradiation of residual agent at the treatment site hopefully produces the desired cytotoxic effect in the diseased tissue. This approach may unfortunately also damage healthy surrounding tissue by undesired but unavoidable activation of residual agent still present in the healthy surrounding tissue. One approach to solving this problem is to couple the radiosensitizer with a moiety capable of providing improved biotargetting of the diseased tissue. This, however, has proven to be very difficult to achieve.

It would also be highly desirable if the radiosensitizer could be used to improve identification of target size, location and depth so that the therapeutic radiation could be more precisely delivered to the target, such as a cancerous tumor. Combined diagnostic use (as a contrast agent) and therapeutic use (as a radiosensitizer) of the agent would reduce risk to the patient by (1) reducing the number of required procedures necessary for diagnosis and treatment, (2) reducing the overall diagnosis and treatment time, and (3) reducing cost.

Accordingly, one object of the present invention is to develop new radiosensitizers that have one or more of the following characteristics: (1) improved light-to-dark cytotoxicity ratio; (2) improved accumulation of agent into diseased tissue with strong contrast between diseased and healthy tissue; (3) rapid clearance from normal tissue; and (4) capability of combined imaging and therapy. Further desirable characteristics include low agent cost, and significant regulatory history (so as to facilitate acceptance by the regulatory and medical communities).

SUMMARY OF THE INVENTION

The present invention is directed to a radiosensitizer agent for treatment of diseased tissue using radiosensitization or ionizing radiation comprising a halogenated xanthene. Preferably, the halogenated xanthene is Rose Bengal or its derivative.

In a further embodiment of the present invention, the radiosensitizer agent also acts as an imaging contrast agent.

The present invention is also directed to a radiosensitizer agent for treatment of diseased tissue using radiosensitization or ionizing radiation wherein the agent exhibits a preference for concentration in biologically sensitive structures in tissue, such as, for example, cellular membranes. Preferably, the agent biologically or chemically targets the biologically sensitive structures.

Further, the present invention is directed to a method for treating diseased tissue.

One embodiment of the method of the present invention includes the steps of administering a radiosensitizer agent, preferably a halogenated xanthene, a portion of radiosensitizer agent being retained in diseased tissue; and treating the diseased tissue with x-rays or other ionizing radiation to activate the radiosensitizer agent in the diseased tissue.

A further embodiment of the method of the present invention includes the step of imaging a patient using the radiosensitizer agent to identify the diseased tissue.

BRIEF DESCRIPTION OF THE DRAWINGS

FIG. 1a is an illustration of the chemical structure of Rose Bengal;

FIG. 1b is an illustration of the chemical structure of a halogenated xanthene;

FIG. 2 illustrates the CAT scan image of test tubes of Rose Bengal, standard x-ray contrast agents and a control;

DETAILED DESCRIPTION OF THE PRESENTLY PREFERRED EMBODIMENTS

Figure 3:
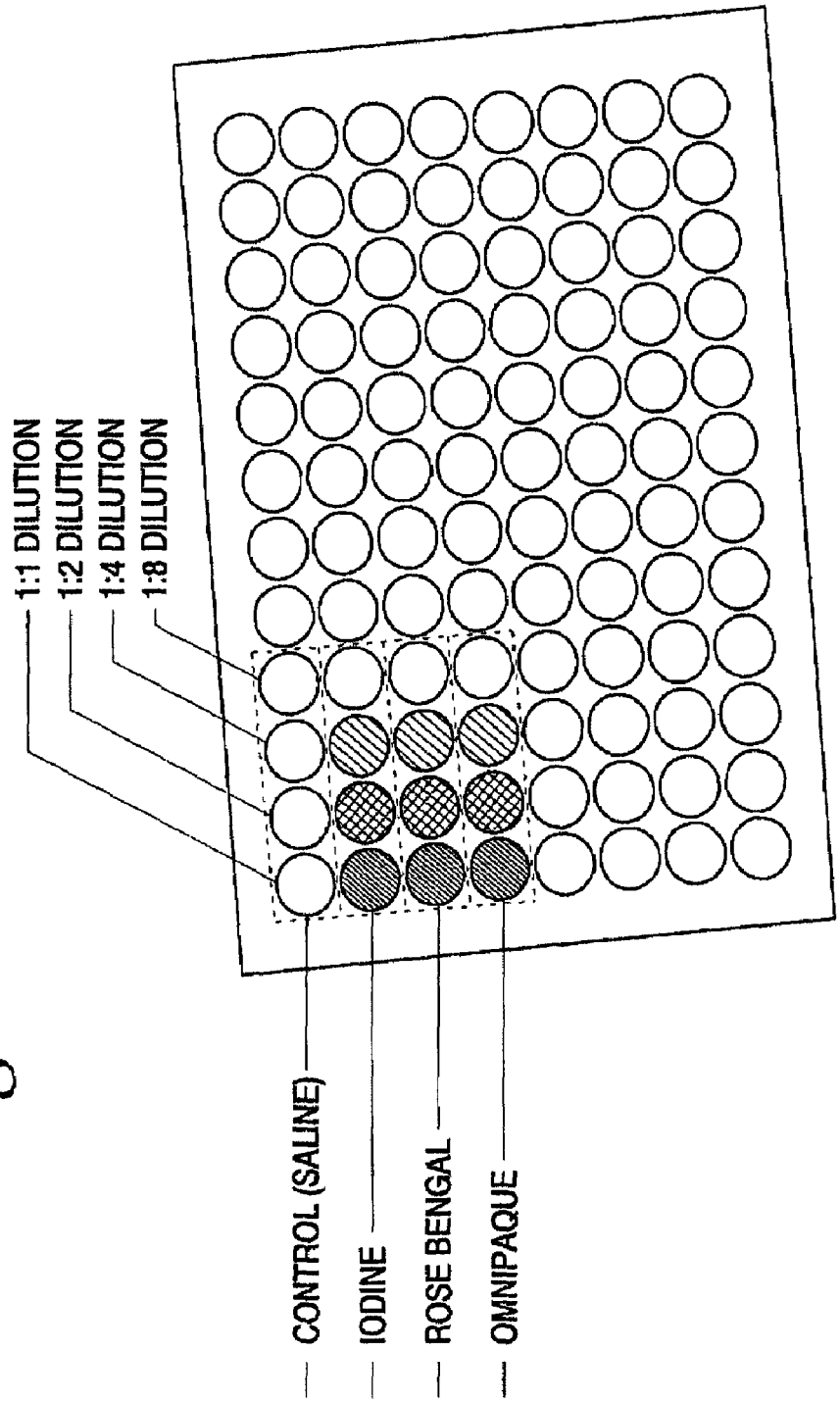
FIG. 3 illustrates a CAT scan of a range of concentrations of the solutions of FIG. 3.

The present invention is directed to agents that can efficiently interact with x-rays or other types of ionizing radiation to produce a beneficial biological response and to methods of treatment and imaging using such agents.

The inventors of the present invention have discovered that radio dense agents, such as the halogenated xanthenes discussed infra, which exhibit a preference for concentration in cellular membranes and other key components and structures of diseased tissue, will exhibit additional therapeutic dose enhancement over that possible with previously known agents or enhancement mechanisms. This additional dose enhancement is a consequence of increased radiosensitization yield of such agents owing to improved proximity of such agents, upon interaction with diseased tissue, to sensitive structures during irradiation and subsequent radiosensitization. Specifically, most radiosensitizers function by absorbing highly-penetrating energy (which in itself has little direct interaction with tissue), and then releasing this energy in a less-penetrating, more cytotoxic form (such as lower-energy re-emission) that is capable of interacting primarily only with proximal, biologically-sensitive structures or materials (such as cellular membranes and genetic material).

Thus, any radiodense agent, such as halogenated xanthenes, that exhibits chemical or biological targeting to such biologically-sensitive structures or materials, and which thereby becomes substantially concentrated in areas in physical proximity to such structures or materials, will increase the overall efficiency of radiosensitization (i.e. conversion of high-energy stimulating excitation into localized cytotoxic effects). This yield enhancement results from the increased probability that proximally-released energy will interact favorably with the sensitive target (before annihilating or otherwise dissipating in an inefficacious manner) whenever the agent responsible for such re-emission is concentrated as close as possible to such a target. Stated in simple terms, the released energy, having a short mean free path, will have a higher probability of interacting with the target if it is emitted from an agent located closer to the target.

Such approaches to radiosensitization enhancement are not taught in the prior art, which are based primarily on permeability-based targeting. In contrast, targeting as taught by the present invention uses the superior approach based on chemical or biological targeting. This type of targeting can be effected by chemical partitioning of the agent at, near or into the target (for example, using an agent that partitions into cell walls, such as Rose Bengal discussed infra, the chemical structure of which is illustrated in FIG. 1a), by controlled agent delivery at, near or into the target (for example by encapsulation of an agent, such as Rose Bengal, into a delivery vehicle, such as a micelle, nanoparticle, or liposome, that interacts preferentially with a target site, such as cell walls, and may adhere, fuse, combine, or otherwise interact in such a way that agent is delivered to the target), or by physically increasing local concentration of agent at, near or into the target, for example by localized delivery via injection, flooding, or spraying.

Preferably, these agents have a large x-ray cross-section, a high light-to-dark cytotoxicity ratio, a preference for accumulation in diseased tissue, low agent cost, rapid clearance from normal tissue, and a significant regulatory history (so as to facilitate acceptance by the regulatory and medical communities).

Applicants have discovered a class of agents that fits this criteria and is preferably used in the present invention. These agents are referred to as halogenated xanthenes and are illustrated in FIG. 1b, where the symbols X, Y, and Z represent various elements present at the designated positions, and the symbols $R^1$ and $R^2$ represent various functionalities present at the designated positions. Chemical and physical properties (such as the chemical constituents at positions X, Y, and Z and the functionalities $R^1$ and $R^2$, along with molecular weight) of representative halogenated xanthenes are summarized in attached Table 1. While many of the halogenated xanthenes are highly soluble in aqueous solution, in general all demonstrate a preference for selective partitioning into hydrophobic environments, such as within cell membranes.

In general, halogenated xanthenes are characterized by a low dark cytotoxicity and chemical properties that are substantially unaffected by the local chemical environment or the attachment of functional derivatives at positions $R^1$ and $R^2$. Moreover, the halogenated xanthenes will target some tumors or other diseased tissues based on their inherent selective partitioning properties.

A specific example of a halogenated xanthene is Rose Bengal (4,5,6,7-tetrachloro-2',4',5',7'-tetraiodofluorescein; see 10 in FIG. 1a). In particular, Rose Bengal has been found to accumulate preferentially in (i.e. target) some tumors and other diseased tissues. Moreover, Rose Bengal has other desirable characteristics such as a negligible dark cytotoxicity, relatively low cost, the ability to clear rapidly from the body, and a partially established regulatory history. Furthermore, the inventors have found that the special chemical properties of Rose Bengal allow it to be dissolved in aqueous solution at high concentrations while retaining a significant preference for hydrophobic environments, such as within cell membranes.

The present inventors have also discovered that the facility with which the halogenated xanthenes target specific tissues or other sites can be optimized by attachment of specific functional derivatives at positions $R^1$ and $R^2$, so as to change the chemical partitioning or biological activity of the agent. For example, attachment of one targeting moiety or more at positions $R^1$ or $R^2$ can be used to improve targeting to specific tissues, such as cancerous tumor tissues or sites of localized infection. These targeting moieties include DNA, RNA, amino acids, proteins, antibodies, ligands, haptens, carbohydrate receptors or complexing agents, lipid receptors or complexing agents, protein receptors or complexing agents, chelators, encapsulating vehicles, short- or long-chain aliphatic or aromatic hydrocarbons, including those containing aldehydes, ketones, alcohols, esters, amides, amines, nitriles, azides, or other hydrophilic or hydrophobic moieties.

An example of this feature would be to combine Rose Bengal with a lipid (at position $R^1$, via esterification, so as to increase the lipophilicity of Rose Bengal, and thereby modify its targeting properties in a patient. Such a modified agent could be administered directly as a micelle suspension, or delivered in conjunction with a delivery vehicle, such as a surfactant, and would exhibit increased targeting to tumor cells. Suitable formulations of such an agent include topical creams and lotions, and liquids for intravenous or parenteral injection.

Figure 4:
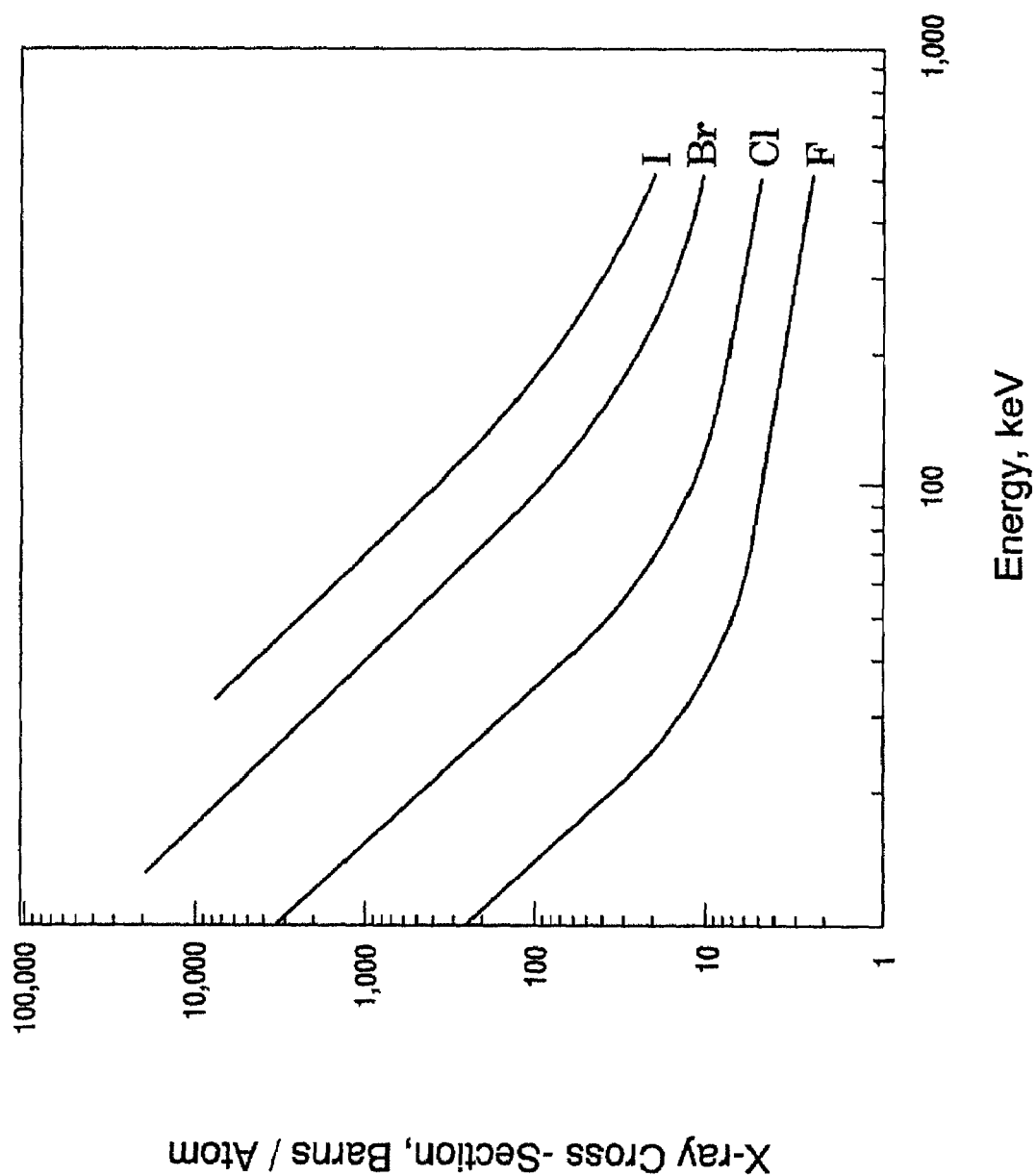
FIG. 4 is a graph of energy versus x-ray cross-section for halogens.

FIG. 4 demonstrates that strong absorption for the halogens of the halogenated xanthenes occurs well below the energies used for standard diagnostic or therapeutic x-ray devices, which generally use energies greater than 30 keV. In fact, the halogen content of the halogenated xanthenes makes this class of agent potent x-ray absorbers, and thus highly suitable as radiosensitizers. Further, since x-ray cross-section increases substantially in the order F<Cl<Br<I, it is preferred that those halogenated xanthenes with a large content of I or Br be used for x-ray sensitization. Furthermore, tests indicate that the presence of I or Br yields enhanced sensitization relative to that possible with other halogens. Therefore, as shown in Table 1, Tetrabromoerythrosin, Rose Bengal, Phloxine B, Erythrosin B, and Eosin Y have larger x-ray cross-sections than Solvent Red or Eosin B as a consequence of respective differences in halogen content, and thereby are preferred for use as x-ray sensitizing agents. More preferably, the high iodine content of Rose Bengal and its derivatives and the additional bromine substitution of 4,5,6,7-Tetrabromoerythrosin and its derivatives, makes these agents the most preferred x-ray sensitizing agents of this class.

Accordingly, in a preferred embodiment of the present invention, at least one halogenated xanthene is used as an x-ray sensitizer or radiosensitizer agent for treatment of diseased tissue using radiosensitization. Prior to radiosensitization, the agent can be administered orally, systemically (e.g. by an injection), or topically, in a manner well known in the art. In a further preferred embodiment of the present invention, Rose Bengal or its derivatives or 4,5,6,7-Tetrabromoerythrosin or its derivatives is the radiosensitizer agent. It is also preferred that x-rays or other ionizing radiation with energy $\geq$ approximately 1 keV and $\leq$1000 MeV be used to activate the agent. Preferably, the agent is activated using x-rays having an energy in excess of 30 keV.

Applicants have also discovered that halogenated xanthenes can be used as an imaging contrast agent for x-ray or other ionizing radiation imaging, such as CAT scan, fluorography or other related procedures. In particular, the inventors have discovered that halogenated xanthenes are particularly proficient as imaging contrast agents because of their large x-ray cross-sections and because their chemical structure, which has a high electron density due to their significant halogen content, renders them opaque to x-rays or other ionizing radiation used for imaging. For example, Rose Bengal is highly opaque to the x-rays used for CAT scan or normal x-ray imaging. FIGS. 2 and 3 illustrate the opaqueness of Rose Bengal versus standard x-ray contrast agents and a control. These figures are drawings of actual pictures of experiments done by the inventors of the present invention. For example, the CAT scan image of test tubes containing various solutions shown in FIG. 2 demonstrates that iodine (350 mgI/mL in aqueous base), Rose Bengal (225 mg halogen/mL in saline), and Omnipaque™ (350 mgI/mL Iohexol) have similar x-ray densities. Furthermore, these densities are dramatically greater than that of a control (saline). A CAT scan image of various dilutions of these same solutions (held in wells in a 96-well sample plate) illustrated in the drawing in FIG. 3 further demonstrates that Rose Bengal shows comparable response to that of the standard x-ray contrast agents across a range of concentrations.

Accordingly, it is a further preferred embodiment of the present invention to use at least one halogenated xanthene agent as an imaging contrast agent for x-ray or ionization radiation based imaging and detection of diseased tissue, and then treat the detected diseased tissue by radiosensitization of the residual agent present in such tissue.

This description has been offered for illustrative purposes only and is not intended to limit the invention of this application, which is defined in the claims below. For example, it will be clear to those of ordinary skill in the art that the targeting described herein for the specific example of the halogenated xanthenes can be adapted or otherwise applied to other radiodense materials, including conventional radiosensitizers.

TABLE I

Physical Properties of Example Halogenated Xanthenes:

| Compound | Substitution | | | | | MW (g) |
|---|---|---|---|---|---|---|
| | X | Y | Z | R¹ | R² | |
| Fluorescein | H | H | H | Na | Na | 376 |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | NO₂ | Br | H | Na | Na | 624 |
| Eosin Y | Br | Br | H | Na | Na | 692 |
| Ethyl Eosin | Br | Br | H | C₂H₅ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| 4,5,6,7-Tetrabromoerythrosin | I | I | Br | Na | Na | 1195 |

We claim:

1. A radiosensitizer agent for treatment of cancer and tumors, said radiosensitizer agent comprising an aqueous solution of a halogenated xanthene, said halogenated xanthene interacting with ionizing radiation applied to said cancer or tumor to enhance the therapeutic efficacy of said ionizing radiation, wherein said halogenated xanthene comprises disodium 4,5,6,7-tetrabromoerythrosin.

2. The radiosensitizer agent of claim 1 wherein said ionizing radiation is approximately greater than or equal to 1 keV and less than or equal to approximately 1000 MeV.

3. The radiosensitizer agent of claim 1 wherein said ionizing radiation comprises x-rays.

4. The radiosensitizer agent of claim 3 wherein said x-rays have an energy between 30 kiloelectron volts and 1000 megaelectron volts.

5. A radiosensitizer agent for treatment of cancer and tumors using ionizing radiation, said radiosensitizer agent comprising an aqueous solution of a halogenated xanthene wherein said halogenated xanthene is activated using x-rays having an energy greater than 30 keV, said halogenated xanthene comprising disodium 4,5,6,7-tetrabromoerythrosin.

6. A radiosensitizer agent for treatment of cancer and tumors, said radiosensitizer agent comprising an aqueous solution of a halogenated xanthene, said halogenated xanthene interacting with ionizing radiation applied to said cancer or tumor to enhance the therapeutic efficacy of said ionizing radiation, wherein said halogenated xanthene comprises 4,5,6,7-tetrabromoerythrosin, wherein at least one biological targeting moiety is attached to said halogenated xanthene to enhance targeting of said halogenated xanthene to biologically sensitive structures of said cancer or tumors.

7. A radiosensitizer agent for treatment of cancer and tumors using radiosensitization or ionizing radiation, said radiosensitizer agent comprising an aqueous solution of a halogenated xanthene wherein said ionizing radiation is approximately greater than or equal to 1 keV and less than or equal to approximately 1000 MeV, said halogenated xanthene comprising disodium 4,5,6,7-tetrabromoerythrosin.

8. The radiosensitizer agent of claim 7 wherein said halogenated xanthene also is an imaging contrast agent.

9. A radiosensitizer agent for treatment of cancer and tumors, said radiosensitizer agent comprising a halogenated xanthene, said halogenated xanthene interacting with ionizing radiation applied to said cancer or tumor to enhance the therapeutic efficacy of said ionizing radiation, wherein at least one biological targeting moiety is attached to said halogenated xanthene to enhance targeting of said halogenated xanthene to biologically sensitive structures of said cancer or tumors.

* * * * *